(12) United States Patent
Sivard

(10) Patent No.: US 8,538,544 B2
(45) Date of Patent: Sep. 17, 2013

(54) IMPLANTABLE RF TELEMETRY DEVICES WITH POWER SAVING MODE

(75) Inventor: Ake Sivard, Solna (SE)

(73) Assignee: Microsemi Semiconductor AB (SE)

( * ) Notice: Subject to any disclaimer, the term of this patent is extended or adjusted under 35 U.S.C. 154(b) by 1450 days.

(21) Appl. No.: 11/388,515

(22) Filed: Mar. 24, 2006

(65) Prior Publication Data

US 2006/0229053 A1   Oct. 12, 2006

(30) Foreign Application Priority Data

Apr. 6, 2005   (GB) .................................. 0506925.7

(51) Int. Cl.
*A61N 1/08* (2006.01)

(52) U.S. Cl.
USPC .............................................. 607/60; 607/32

(58) Field of Classification Search
USPC ................................................ 607/16, 32, 60
See application file for complete search history.

(56) References Cited

U.S. PATENT DOCUMENTS

| | | | |
|---|---|---|---|
| 4,519,401 A | 5/1985 | Ko et al. | |
| 6,073,050 A * | 6/2000 | Griffith | 607/57 |
| 6,443,891 B1 * | 9/2002 | Grevious | 600/302 |
| 2001/0041551 A1 | 11/2001 | Rotzoll | |
| 2002/0065540 A1 * | 5/2002 | Lebel et al. | 607/60 |
| 2002/0173702 A1 * | 11/2002 | Lebel et al. | 600/300 |
| 2003/0149459 A1 | 8/2003 | Von Arx et al. | |
| 2003/0187484 A1 * | 10/2003 | Davis et al. | 607/60 |
| 2004/0049246 A1 * | 3/2004 | Almendinger et al. | 607/60 |
| 2005/0222645 A1 * | 10/2005 | Malave et al. | 607/60 |
| 2007/0049991 A1 * | 3/2007 | Klostermann et al. | 607/60 |
| 2007/0167994 A1 * | 7/2007 | Shelton et al. | 607/60 |

FOREIGN PATENT DOCUMENTS

| | | |
|---|---|---|
| WO | WO 03/053515 A1 | 7/2003 |
| WO | 03/066163 A3 | 8/2003 |
| WO | WO 03/066163 A1 | 8/2003 |
| WO | WO 03/084606 A2 | 10/2003 |
| WO | 2005/099817 A1 | 10/2005 |

* cited by examiner

*Primary Examiner* — Kennedy Schaetzle
*Assistant Examiner* — Erica Lee
(74) *Attorney, Agent, or Firm* — Laubscher & Laubscher, P.C.

(57) ABSTRACT

An electronic implantable device with a power saving circuit incorporates a radio frequency receiver with high power consumption. The first power radio receiver of high power is normally turned off during a period of inactivity. When an analyzer forming part of a second radio receiver and coupled to the first radio receiver detects a predetermined identification code in a received radio frequency signal received by the second radio receiver, it outputs a signal to turn on the first power receiver.

23 Claims, 1 Drawing Sheet

IMPLANTABLE RF TELEMETRY DEVICES WITH POWER SAVING MODE

BACKGROUND OF THE INVENTION

1. Field of the Invention

This invention describes a method of saving power in an implantable device, such as a pacemaker, which includes RF telemetry functionality.

2. Description of Related Art

Since the allocation of a special frequency band for implantable medical devices using RF telemetry, the so-called MICS (Medical Implantable Communication Service) band, by FCC in the late 1990's, the development of devices including this functionality has really taken off. However, since the battery capacity in an implantable device is very limited, the introduction of a RF transceiver operating at 402-405 MHz becomes a real challenge. If the transceiver operates at 5 mA in the active mode, this might be acceptable since in the normal user scenario the on-time is only a fraction (<0.01%) of the total device life time. A trickier problem is the issue of waking up the RF component from the off state to start communications in a reasonable amount of time without draining the battery.

The most common method of solving this problem today is to introduce the so-called sniff mode. This means that the complete receiver RF portion of the device is turned on for a limited period of time (e.g. 10 milliseconds) during which time the device listens to see if there are any transmitters active in the vicinity wanting to make contact. By duty cycling the on (sniff) time heavily with the off time a considerable power saving can be achieved. For example having the device on for 5 ms consuming 5 mA and then off for 995 ms while consuming only leakage current of maybe 100 nA will lower the average current consumption to only about 25 μA. This is very good in most applications. However, for an implantable device consuming less than 10 μA in total this is unacceptable. Lowering the average power consumption further by decreasing the on time is difficult since a certain time is needed to start up the RF receiver and to receive a message telling the device to start transmitting a response. Increasing the off time is not preferred since the doctor who is trying to get in contact with the device expects a response within a second or two.

An example of the prior art is found in U.S. Pat. No. 4,519,401 issued May 28, 1985.

SUMMARY OF THE INVENTION

According to the present invention there is provided an implantable electronic device, comprising a first radio receiver for receiving telemetry data, said first radio receiver having a wake mode and a sleep mode, and being configured to be in said sleep mode unless woken up by a triggering event; a second radio receiver with very low power consumption compared to said first radio receiver; a control unit coupled to the second radio receiver for periodically turning on the second radio receiver during a listen window to listen for an incoming radio frequency signal indicating an external device wishes to establish contact; an analyzer forming part of the second radio receiver for verifying the properties of an incoming radio signal, said analyzer, in response to receipt of said incoming radio frequency signal, prolonging the listening window to enable reception of a full wake-up message, wherein the prolongation of the listen window is sustained only as long as the properties of the incoming wake-up message match a correct message ; and said analyzer further being configured to place said first radio receiver in the wake mode to receive incoming telemetry data in response to the detection of a full correct wake-up message by the second radio receiver.

The first radio receiver normally forms part of a transceiver for exchanging two-way telemetry data with an external device.

Thus, in accordance with the invention, an implantable device with an RF telemetry transceiver has a separate low power receiver to wake-up the device to save power when an external RF unit wishes to communicate with the implanted device. The normal RF telemetry transceiver is turned off for most of the time except when there is an active telemetry link in operation.

The low power receiver has a simplified architecture to drive down the power consumption to about 200 μA and operates as a wake-up device for the full RF transceiver. Because of the simplicity of the low power receiver it can also be turned on very quickly (less than 200 μs).

For most of the time all the RF functionality in the implantable device is switched off and consumes less than 100 nA of leakage current. Every 1 second the lower power receiver is turned on by the application circuitry for about 0.5 ms to listen to see if there are any outside devices trying to get in contact. If an appropriate signal is received, the listen window is prolonged to enable the reception of a full wake-up message and trigger the turn on of the full-blown MICS transceiver, which starts to transmit and receive. The prolongation of the wake-up receiver's reception window is only sustained as long as the properties of the received message match a correct message. One example of such a property is to use so called Manchester encoding and to turn off the low power receiver as soon as any non-Manchester encoded signal is detected. This leads to additional power saving since the wake-up receiver is turned off immediately as soon as it becomes clear that the message is incorrect instead of receiving a complete wake-up message before checking if the message is correct or not.

With a power consumption of 200 μA from the low power receiver this will give a total average power consumption of 200 nA (100 nA leakage and 100 nA from the low power receiver).

In accordance with another aspect the invention provides a method of saving power in an implantable electronic device having a first radio receiver for receiving telemetry data, said first radio receiver having a wake mode and a sleep mode, and being configured to be normally in said sleep mode, said method comprising periodically listening in a sniff mode for a wake-up signal with a second radio receiver that has very low power consumption compared to said first radio receiver; in response to reception of part of a wake-up signal by said second radio receiver prolonging the sniff mode while the received part of a wake-up signal remains valid until a complete wake-up signal is received; and in response to a complete valid wake-up signal, placing said first radio receiver in the wake mode to receive incoming telemetry data.

BRIEF DESCRIPTION OF THE DRAWINGS

The invention will now be described in more detail, by way of example only, with reference to the accompanying drawings, in which:—

DETAILED DESCRIPTION OF THE PREFERRED EMBODIMENT

Figure 1:
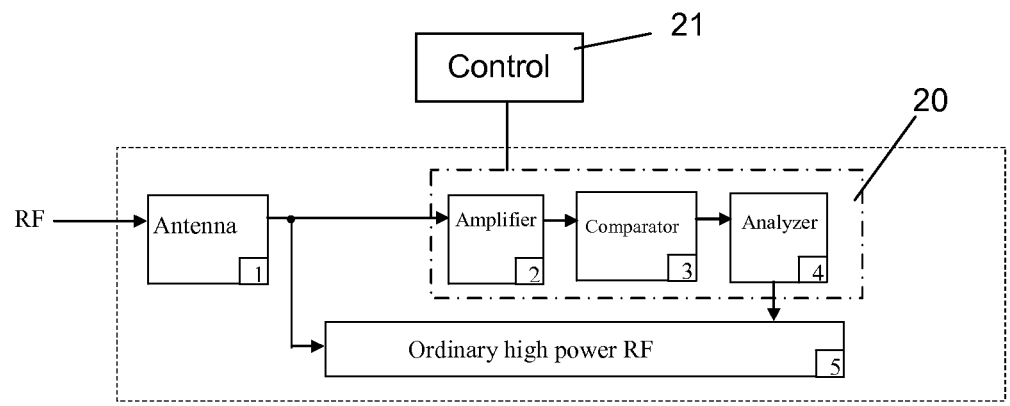
FIG. 1 is a block diagram of an implantable device in accordance with one embodiment of the invention.

Referring to FIG. 1, the simplified receiver comprises an antenna 1 receiving a wake-up signal (common with the MICS band antenna or separate), an amplifier 2 which amplifies the signal, and a comparator/detector 3 that detects the amplified signal if it is above a certain power level.

To further increase the security of the receiver against the device being woken up by noise, the wake-up signal comprises a predetermined coded pattern, which is analyzed in an analyzer 4 to see if it matches the wake-up pattern. Only if the pattern is correct the full transceiver 5 will be turned on by the analyzer 4. The amplifier 2, comparator 3 and analyzer 4 form part of a simple very low power receiver 20, which is periodically turned on during a sniff period to listen for an incoming radio frequency signal by a control unit 21.

Figure 2:
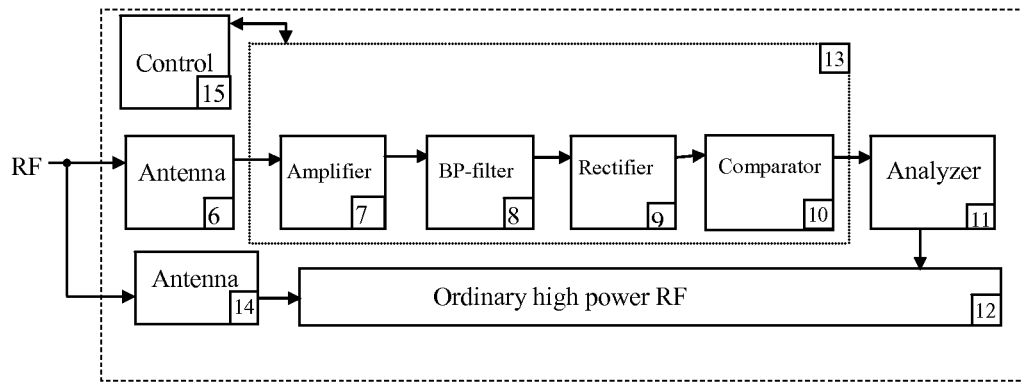
FIG. 2 is a more detailed block diagram of an embodiment of the invention.

FIG. 2 shows another embodiment where an RF signal is received by a tuned antenna 6 connected to an amplifier 7, an optional band pass filter 8, which in turn is connected to a rectifier 9, connected to a comparator 10, which is connected to an analyzer 11. The analyzer 11 is connected to the full high power RF transceiver 12. The amplifier 7, the band pass filter 8, the rectifier 9, the comparator 10 form part of a simple low power RF receiver circuit 13. The control block 15 controls the turning on and turning off of the low power receiver 13.

The full transceiver may use the same antenna as the low power receiver as shown in FIG. 1 or may use a separate antenna as shown in FIG. 2 with antenna 14 shown as a separate entity.

The incoming RF signal picked up by the antenna 6 is fed into the simple receiver circuit 13. The described solution uses a Manchester encoded On/Off Keying (OOK) modulation scheme, but other modulation schemes such as Frequency Shift Keying (FSK), Phase Shift Keying (PSK), etc. can also be envisioned for those skilled in the art.

The signal picked up by the antenna is amplified by the amplifier 7, fed into the low power band-pass filter 8 that filters the signal around the chosen wake-up frequency, in or outside the MICS band. The filtered signal is then fed into the rectifier 9 and connected to the comparator 10 as a much lower frequency signal. The comparator 10 acts as a decoder that decodes the incoming RF-signal (if any), and if the level is above the comparators threshold, which can be made programmable, starts to convert the signal into logical ones '1' and zeros '0'. The digital signal from the comparator 10 is fed into an analyzer 11 where it checked to see if it is a Manchester encoded signal and if so is compared to a predetermined digital signal pattern and if the incoming signal matches this pattern the analyzer turns on the full RF transceiver, which starts the full RF transmission. If there is no matching Manchester encoded signal detected within the 0.5 ms window the device just goes back to sleep until the next 0.5 ms on time 995.5 ms later.

For greater noise immunity it is an preferable to code the incoming signal using a more sophisticated scheme than one where the presence of signal represents a '1' and absence of signal represents a '0'. Examples include pulse width modulation (PWM) where a long presence of a signal in a time slot represents a '1' and a short presence represents a '0'. Alternatively the signal may be amplitude modulated using Pulse Position Modulation (PPM) or Pulse Amplitude Modulation (PAM), provided a suitable analyzer 14 is used.

An additional level of security can be achieved by letting the detection of the correct signal within the first 5 ms trigger a prolongation of the low power receiver to allow a longer coding pattern to be used before turning on the full transceiver. In this embodiment the prolongation only continues as long as the received pattern is Manchester code and thus matches the expected properties. However, those skilled in the art will appreciate that the said expected properties can mean any coding pattern as well as the correct pulse width, correct pulse position, correct frequency, correct pulse amplitude etc. This is done even before the digital wake-up message is decoded given the possibility of immediately going back to sleep as soon as the incoming message has the incorrect properties.

The simplicity of the receiver 13 makes it very difficult to achieve very good receiver sensitivity. In order to attain a reasonable wake-up range it can be advantageous to use another frequency band than the MICS band, which is very limited in the allowed output power (maximum 25 μW). Examples of such frequency bands that can be used are the ISM band at 2.45 GHz, the US ISM band at 902-928 MHz, the Short Range devices band at 868 MHz in Europe. These bands all have a much higher power limit than the MICS band.

The described circuitry lends itself to integration in a single chip, for example, using CMOS technology.

It will be appreciated by one skilled in the art that the above description represents an exemplary embodiment, and that many variants within the scope of the appended claims are possible without departing from the scope of the invention.

The invention claimed is:

1. An implantable electronic device, comprising:
   a first radio receiver for receiving telemetry data, said first radio receiver having a wake mode and a sleep mode, and being configured to be in said sleep mode unless woken up by a triggering event;
   a second radio receiver with very low power consumption compared to said first radio receiver;
   a control unit coupled to the second radio receiver and configured to periodically turn on the second radio receiver for a listen window to listen for a radio frequency signal containing a wake-up message indicating an external device wishes to establish contact, wherein the listen window is shorter than the duration of a complete wake-up message;
   an analyzer forming part of the second radio receiver and configured to verify the properties of a received portion of the wake-up message in a listen window by matching the received portion of said wake-up message with predetermined properties, and said analyzer, in response to a match of the received portion of said incoming wake-up message with said predetermined properties, prolonging the listen window to receive a remaining portion of the incoming wake-up message for as long as the received portion of said incoming wake-up message continues to match said predetermined properties until the complete wake-up message is received; and
   said analyzer further being configured to create said triggering event to place said first radio receiver in the wake mode to receive incoming telemetry data in response to the detection of the complete wake-up message by the second radio receiver.

2. An implantable electronic device as claimed in claim 1, wherein said predetermined properties comprise a predetermined identification code.

3. An implantable electronic device as claimed in claim 2, wherein said analyzer is responsive to an identification code modulated using on/off keying.

4. An implantable electronic device as claimed in claim 2, wherein said analyzer is responsive to an identification code modulated using frequency shift keying.

5. An implantable electronic device as claimed in claim 2, wherein said analyzer is responsive an identification code modulated using amplitude shift keying.

6. An implantable electronic device as claimed in claim 2, wherein said analyzer is responsive an identification code is modulated using phase shift keying or any variant thereof.

7. An implantable electronic device as claimed in claim 2, wherein said identification code is pulse width modulated, and said analyzer is configured to detect said pulse width modulation.

8. An implantable electronic device as claimed in claim 2, wherein said identification code is pulse position modulated, and said analyzer is configured to detect amplitude pulse position modulation.

9. An implantable electronic device as claimed in claim 2, wherein said identification code is pulse amplitude modulated, and said analyzer is configured to detect said pulse amplitude modulation.

10. An implantable electronic device as claimed in claim 1, wherein said first radio receiver forms part of a transceiver for receiving and transmitting telemetry data.

11. An implantable electronic device as claimed in claim 1, wherein said first and second radio frequency receivers share a common antenna.

12. An implantable electronic device as claimed in claim 1, wherein first radio receiver has a separate antenna from said second radio receiver.

13. An implantable electronic device as claimed in claim 1, wherein said first radio receiver operates in a different frequency band from said second radio receiver.

14. An implantable electronic device as claimed in claim 1, wherein said predetermined properties comprise Manchester code, and the prolongation of the listen window is terminated as soon as any non-Manchester coded signal is detected.

15. An implantable electronic device as claimed in claim 1, wherein said properties of the incoming signal comprise Return-To-Zero code.

16. An implantable electronic device as claimed in claim 1, wherein said properties of the incoming signal comprise the delay between two symbols.

17. An implantable electronic device as claimed in claim 1, wherein said predetermined properties comprise a predetermined frequency window.

18. An implantable electronic device as claimed in claim 1, wherein said predetermined properties comprise a predetermined amplitude window.

19. An implantable electronic device as claimed in claim 1, wherein said predetermined properties comprise a predetermined pulse position window.

20. An implantable electronic device as claimed in claim 1, wherein said second receiver with low power consumption receiver comprises an amplifier, a band pass filter, a rectifier and a comparator.

21. A method of saving power in an implantable electronic device having a first radio receiver for receiving telemetry data, said first radio receiver having a wake mode and a sleep mode, and being configured to be in said sleep mode unless woken up by a triggering event, said method comprising:
   periodically listening for a listen window with a second radio receiver that has very low power consumption compared to said first radio receiver for an incoming radio frequency signal containing a wake-up message indicating an external device wishes to establish contact, wherein the listen window is shorter than the duration of a complete wake-up message;
   the second receiver in response to reception of a partial wake-up message matching predetermined properties, prolonging the listen window to receive a remaining portion of the incoming wake-up message for as long as the received portion of said incoming wake-up message continues to match said predetermined properties until a complete wake-up message is received; and
   the second receiver in response to reception of the complete wake-up message, creating said triggering event to place said first radio receiver in the wake mode to receive incoming telemetry data.

22. A method as claimed in claim 21, wherein said predetermined properties comprise a predetermined identification code, and said first radio receiver is placed in the wake mode in response to detection of said predetermined identification code.

23. A method as claimed in claim 21, wherein said second radio receiver is normally in sleep mode and is woken at intervals to listen for said wake-up message.

* * * * *